United States Patent [19]
Kashiwakuma et al.

[11] Patent Number: 5,871,904
[45] Date of Patent: Feb. 16, 1999

[54] IMMUNASSAY OF NON-A, NON-B HEPATITIS VIRUS-RELATED ANTIGENS, MONOCLONAL ANTIBODIES FOR USE THEREIN, AND HYBRIDOMAS PRODUCING THE ANTIBODIES

[75] Inventors: Tomiko Kashiwakuma, Itabashi-ku; Shintaro Yagi, Iruma-gun; Akira Hasegawa, Sakado; Tadahiro Kajita, Nishinomiya; Yohsuke Ohta, Kobe; Hiroyuki Mori, Osaka, all of Japan

[73] Assignees: The Tokyo Metropolitan Institute of Medical Science, Tokyo, Japan; International Reagent Corporation, Hyogo-ken, Japan; Tonen Corporation, Tokyo, Japan

[21] Appl. No.: 501,195

[22] Filed: Jul. 11, 1995

[30] Foreign Application Priority Data

Jul. 12, 1994 [JP] Japan .................................. 6-183904

[51] Int. Cl.$^6$ .............................. C12Q 1/70; C12N 5/12; C07K 16/08; C12P 21/08
[52] U.S. Cl. ......................... 435/5; 435/7.1; 435/240.26; 435/240.27; 530/388.1; 530/388.3
[58] Field of Search .......................... 435/5, 7.1, 240.26, 435/240.27; 530/388.1, 388.3

[56] References Cited

U.S. PATENT DOCUMENTS

| 5,372,928 | 12/1994 | Miyamura et al. | 435/5 |
| 5,437,974 | 8/1995 | Ryan et al. | 435/5 |

FOREIGN PATENT DOCUMENTS

| 0 468 657 A2 | 7/1991 | European Pat. Off. . |
| 0 468 657 | 1/1992 | European Pat. Off. . |
| 0 537 856 A1 | 10/1992 | European Pat. Off. . |
| 0 537 856 | 4/1993 | European Pat. Off. . |
| 0 586 065 A2 | 7/1993 | European Pat. Off. . |
| 42 09 215 | 1/1993 | Germany . |
| WO 92/07001 | 4/1992 | WIPO . |
| WO 92/08738 | 5/1992 | WIPO . |
| WO 92/13892 | 8/1992 | WIPO . |
| 92/22571 | 12/1992 | WIPO . |
| WO 93/04084 | 3/1993 | WIPO . |
| WO 93/04205 | 3/1993 | WIPO . |
| WO 93/06488 | 4/1993 | WIPO . |
| WO 94/14974 | 7/1994 | WIPO . |

OTHER PUBLICATIONS

Geysen et al., "Cognitive Features of Continuous Antigenic Determinants", J. Mol. Recognit. 1(1)323–41 (1988).
Takahashi et al., "Demonstration of a hepatitis C virus-specific antigen predicted from the putative core gene in the circulation of infected hosts", J. Gen. Virol. 73, 667–672 (1992).
Siemonett, et al., *Hybridoma* vol. 13, No. 1, pp. 9–13 (1994).
Hiramatsu, et al., *Hepatology*, vol. 16, No. 2, pp. 306–311 (1992).
Takahashi, et al., *J. of Gen. Virol.*, vol. 73, No. 3, pp. 667–672 (1992).
Kashiwakuma, et al., *J. of Immun. Methods*, vol. 190, No. 1, pp. 79–89 (1996).

*Primary Examiner*—Marian C. Knode
*Assistant Examiner*—Mary K. Zeman
*Attorney, Agent, or Firm*—David G. Conlin; David S. Resnick; Dike, Bronstein, Roberts & Cushman, LLP

[57] ABSTRACT

This invention concerns a monoclonal antibody having binding specificity for an antigenic determinant site on core structural protein from Non-A,Non-B hepatitis virus (NANBV); a hybridoma cell line capable of producing the monoclonal antibody; a process for the preparation of the monoclonal antibody; an immunoassay of NANBV-related antigens by use of the monoclonal antibody; and a test kit for use in the immunoassay. The preferred monoclonal antibody is 5E3, 5F11, 515S or 1080S. The monoclonal antibody can specifically recognize the NANBV core structural protein in sera from patients with Non-A,Non-B hepatitis thereby being served extensively as an antibody in various immunological reagents for definitive diagnosis of Non-A, Non-B hepatitis.

7 Claims, 6 Drawing Sheets

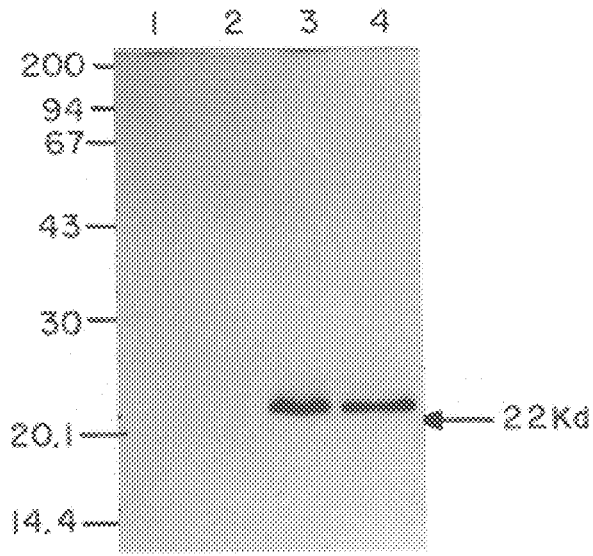
FIG. IA
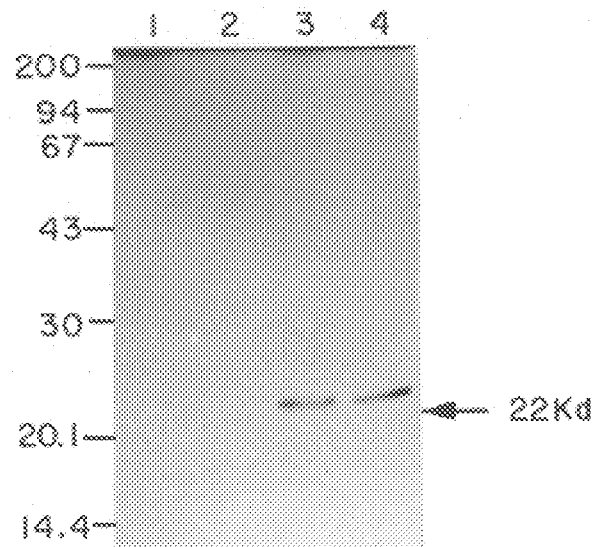
FIG. IB

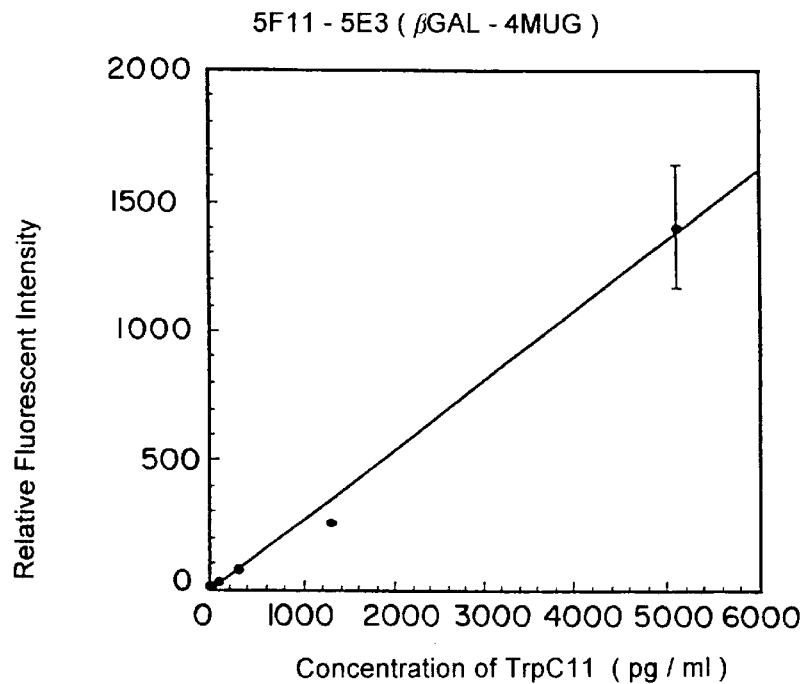
F I G. 6
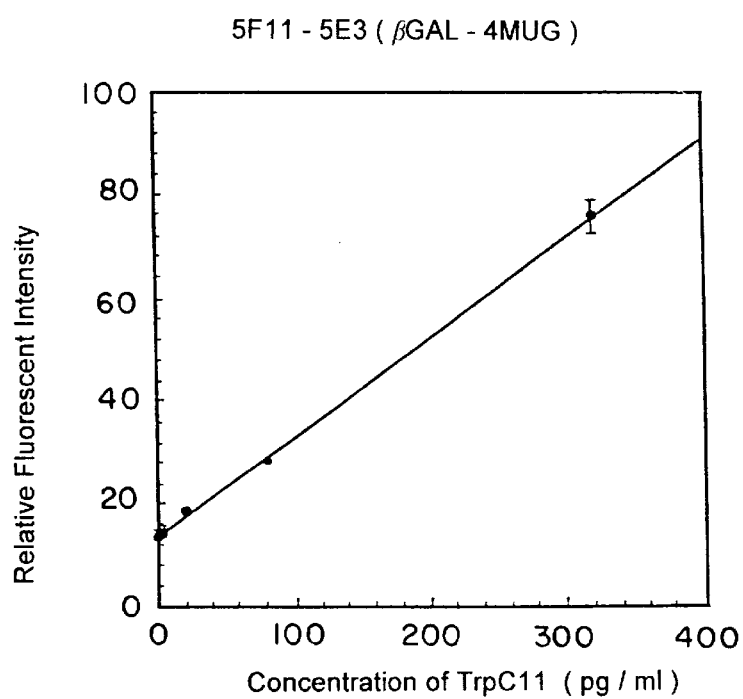
F I G. 7

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 140 amino acids
        ( B ) TYPE: amino acid
        ( C ) STRANDEDNESS:
        ( D ) TOPOLOGY: linear (i i) MOLECULE TYPE: peptide (v i) ORIGINAL SOURCE:
    (A) ORGANISM: NON-A,NON-B hepatitis virus (x i) SEQUENCE DESCRIPTION: SEQ ID NO:1:

```
Met Lys Ala Ile Phe Val Leu Lys Gly Ser Leu Asp Arg Asp Pro Glu
 1               5                  10                 15
Phe Met Gly Thr Asn Pro Lys Pro Gln Arg Lys Thr Lys Arg Asn Thr
             20                  25                 30
Asn Arg Arg Pro Gln Asp Val Lys Phe Pro Gly Gly Gly Gln Ile Val
         35                  40                 45
Gly Gly Val Tyr Leu Leu Pro Arg Arg Gly Pro Arg Leu Gly Val Arg
     50                  55                 60
Ala Thr Arg Lys Thr Ser Lys Arg Ser Gln Pro Arg Gly Gly Arg Arg
 65                  70                 75                 80
Pro Ile Pro Lys Asp Arg Arg Ser Thr Gly Lys Ser Trp Gly Lys Pro
                 85                  90                 95
Gly Tyr Pro Trp Pro Leu Tyr Gly Asn Glu Gly Leu Gly Trp Ala Gly
             100                 105                110
Trp Leu Leu Ser Pro Arg Gly Ser Arg Pro Ser Trp Gly Pro Thr Asp
         115                 120                125
Pro Arg His Arg Ser Arg Asn Val Gly Lys Val Ile
     130                 135                140
```

(2) INFORMATION FOR SEQ ID NO:2:

(i) SEQUENCE CHARACTERISTICS:
        (A) LENGTH: 123 amino acids
        (B) TYPE: amino acid
        (C) STRANDEDNESS:
        (D) TOPOLOGY: linear (i i) MOLECULE TYPE: peptide (v i) ORIGINAL SOURCE:
        (A) ORGANISM: NON-A,NON-B hepatitis virus (x i) SEQUENCE DESCRIPTION: SEQ ID NO:2:

```
Met Gly Thr Asn Pro Lys Pro Gln Arg Lys Thr Lys Arg Asn Thr Asn
 1               5                  10                 15
Arg Arg Pro Gln Asp Val Lys Phe Pro Gly Gly Gly Gln Ile Val Gly
             20                  25                 30
Gly Val Tyr Leu Leu Pro Arg Arg Gly Pro Arg Leu Gly Val Arg Ala
         35                  40                 45
Thr Arg Lys Thr Ser Lys Arg Ser Gln Pro Arg Gly Gly Arg Arg Pro
     50                  55                 60
Ile Pro Lys Asp Arg Arg Ser Thr Gly Lys Ser Trp Gly Lys Pro Gly
 65                  70                 75                 80
Tyr Pro Trp pro Leu Tyr Gly Asn Glu Gly Leu Gly Trp Ala Gly Trp
                 85                  90                 95
Leu Leu Ser Pro Arg Gly Ser Arg Pro Ser Trp Gly Pro Thr Asp Pro
             100                 105                110
Arg His Arg Ser Arg Asn Val Gly Lys Val Ile
         115                 120
```

(2) INFORMATION FOR SEQ ID NO:3:

(i) SEQUENCE CHARACTERISTICS:
        (A) LENGTH: 11 amino acids

```
            ( B ) TYPE: amino acid
            ( C ) STRANDEDNESS:
            ( D ) TOPOLOGY: linear ( i i ) MOLECULE TYPE: peptide ( v i ) ORIGINAL SOURCE:
            ( A ) ORGANISM: NON-A,NON-B hepatitis virus ( x i ) SEQUENCE DESCRIPTION: SEQ ID NO:3:

Pro  Gly  Gly  Gly  Gln  Ile  Val  Gly  Gly  Val  Tyr
 1                  5                        10
```

( 2 ) INFORMATION FOR SEQ ID NO:4:

```
    ( i ) SEQUENCE CHARACTERISTICS:
            ( A ) LENGTH: 21 amino acids
            ( B ) TYPE: amino acid
            ( C ) STRANDEDNESS:
            ( D ) TOPOLOGY: linear ( i i ) MOLECULE TYPE: peptide ( v i ) ORIGINAL SOURCE:
            ( A ) ORGANISM: NON-A,NON-B hepatitis virus ( x i ) SEQUENCE DESCRIPTION: SEQ ID NO:4:

Ile  Val  Gly  Gly  Val  Tyr  Leu  Leu  Pro  Arg  Arg  Gly  Pro  Arg  Leu  Gly
 1                  5                        10                       15

Val  Arg  Ala  Thr  Arg
                 20
```

( 2 ) INFORMATION FOR SEQ ID NO:5:

```
    ( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( v i ) ORIGINAL SOURCE:
            ( A ) ORGANISM: NON-A,NON-B hepatitis virus ( x i ) SEQUENCE DESCRIPTION: SEQ ID NO:5:

Lys  Thr  Ser  Lys  Arg  Ser  Gln  Pro  Arg  Gly
 1                  5                        10
```

( 2 ) INFORMATION FOR SEQ ID NO:6:

```
    ( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid ( x i ) SEQUENCE DESCRIPTION: SEQ ID NO:6:

GAATTCATGG  GCACGAATCC  TAAA                                              2 4
```

( 2 ) INFORMATION FOR SEQ ID NO:7:

```
    ( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: other nucleic acid
```

( x i ) SEQUENCE DESCRIPTION: SEQ ID NO:7:

TTAGTCCTCC AGAACCCGGA C                                         21

IMMUNASSAY OF NON-A, NON-B HEPATITIS VIRUS-RELATED ANTIGENS, MONOCLONAL ANTIBODIES FOR USE THEREIN, AND HYBRIDOMAS PRODUCING THE ANTIBODIES

BACKGROUND OF THE INVENTION

1. Field of the Invention

This invention relates to an immunoassay for detecting or quantifying core proteins of the structural region of Non-A, Non-B hepatitis virus in specimens, to monoclonal antibodies for use in the immunoassay, to hybridomas capable of producing the monoclonal antibodies, and to a test kit comprising the monoclonal antibodies.

2. Prior Art

Post-transfusion hepatitis refers literally to a hepatitis caused by transfusion. As a causative virus of the post-transfusion hepatitis, hepatitis B virus (i.e., HBV) was first identified, but it was suspected thereafter that an other virus was involved in the post-transfusion hepatitis in addition to HBV. This virus that is different from HBV was named Non-A,Non-B hapatitis virus (hereinafter, referred to as "NANBV") or hepatitis C virus (i.e., HCV), and its identification was demanded.

Non-A,Non-B hepatitis corresponds to at least 90% of the post-transfusion hepatitis, and 50–80% of the infected patients indicate chronic symptoms which subsequently transfer to cirrhosis then hepatoma in high proportions, and because of this, there has been a great demand on physiological functions of this disease. The Non-A,Non-B hapatitis has been clinically identified mainly by the so-called exclusion-diagnosis method in which it is first confirmed whether this disease is hapatitis A or hepatitis B or other hepatitis caused by known viruses (e.g., cytomegalovirus and Epstein-Barr virus) by which liver disorders are caused, after which if the disease is other than the known hepatitis then it is determined as being Non-A,Non-B hepatitis.

The cloning of a gene of the virus in question was thereafter carried out by a group of Choo et al. using NANBV-infected chimpanzee plasmas (see Science 244:359–362, 1989), and a method for the diagnosis of the Non-A,Non-B hapatitis was developed in which the detection of antibodies raised against NANBV was carried out by use of recombinant antigens prepared by introducing parts of the non-structural region of NANBV genes (i.e., extending from NS3 to NS4) (see Science 244:362–364, 1989; and JP-A-2-500880).

The commercially available first generation reagent that contains a recombinant antigen (i.e., c100-3 protein) developed by Chiron Corp. (USA) can detect as positive 70–80% of patients with chronic Non-A,Non-B hapatitis, but because the c100-3 antibody titer does not rise at the early infection and the detection of the antibody to c100-3 is impossible, it was known that there were cases undetected even when infected and that considerably non-specific responses were observed in sera from patients with autoimmune diseases or hyper-$\gamma$ globulin sera.

More recently, the second generation regents containing an additional core antigen which is a structural protein of NANBV were developed whereby about 90% of patients infected with NANBV could be detected, but the detection of patients with sporadic Non-A,Non-B hepatitis is as low as about 40%. In addition to the above-mentioned antibody-detection methods, developed are methods for the detection of NANBV genes in which the presence or absence of the NANBV genes is determined by PCR (see Science 230:1350–1354, 1985) or DNA probe method.

However, there are some difficult problems in the detection methods using the PCR method. As such problems, the following are exemplified: reverse transcription is required because NANBV is a RNA virus; the loss of cDNA occurs during the reverse transcription; specific amplification equipments are needed; it is impossible to treat a lot of samples at one time because the operation is complex; and contamination of samples are often observed.

Regarding Non-A, Non-B hapatitis virus, its viral level is very low in patient bodies and its in vitro proliferation system has not been established, so no experimental immunological sera have been obtained using native NANBV virions or purified NANBV proteins. Human sera include different productions of antibodies to NANBV-related antigens depending on individuals, namely, individuals showing a high antibody titer, individuals not capable of eliciting the antibodies, and individuals having an antibody to an antigen present in a certain region of NANBV but not any antibodies to antigens in other regions. Additionally, because of polyclonal antibodies, human sera include antibodies to foreign substances other than NANBV, so estimation of obtained results has to be conducted while taking undesirable cross-reactions into consideration.

When unknown antigens are estimated by use of antibodies, well attention is required for the above reasons. In this context, the development of a method of the detection of NANBV itself for definitive diagnosis has been noted.

With respect to monoclonal antibodies to NANBV, prior arts do not describe any practical production of such monoclonal antibodies although its possibility has been suggested (see EP-B-318,216 and EP-B-388,232), except for monoclonal antibodies specific for epitopes on core proteins of NANBV (see JP-A-5-260960). But the latter monoclonal antibodies differ from the monoclonal antibodies of this invention in recognizable epitope types, assay methods, sensitivities for detection, preparation methods, etc.

A high degree of mutation are observed in a Non-A, Non-B hepatitis virus genome as other class of RNA viruses. As stated above, the level of NANBV virions themselves are very low in patients infected with NANBV and thus the level of antibodies to NANBV-related antigens in the patients' sera is low, so all the patients can not be detected using reagents for detection of the antibodies. Because Non-A, Non-B hepatitis whose prevention has not yet been achieved is assumed to transfer to cirrhosis and hepatoma up to 10–30 years after infection in many infected persons (including carriers), early finding and early treatment are of course very important. Recently, it has been reported that the interferon (referred to as "IFN", hereinafter) therapy is effective for chronic patients, but the liver disorders can not be completely cured by the INF treatment alone, as seen from the fact that there are many cases re-suffering from the hepatitis even when the IFN treatment was terminated. Thus complete exclusion of NANBV from the patient bodies is difficult. It is rather significant to grasp the pathology of the disease in order to assume the treatment or prognosis, and because of this, it is strongly desired not only to detect antibodies to NANBV-related antigens but also to measure NANBV-related markers (i.e., antigens). Thus, the development of a method of obtaining NANBV virions, particularly NANBV-related antigens from infected sera in a simple way and in a high yield, as well as the detection or quantitative analysis of the virions or antigens, has been demanded.

SUMMARY OF THE INVENTION

Accordingly, an object of this invention is to provide a method for the simple treatment of NANBV-related antigens to concentrate and then denature them in specimens.

Another object of this invention is to provide a monoclonal antibody which can specifically recognize an NANBV-related core antigen and has a binding constant $K_A$ of $5\times10^7$ [$M^{-1}$] or larger when forming an immune complex between the monoclonal antibody and the NANBV-related core antigen; a hybridoma capable of producing the monoclonal antibody; and a method for the preparation of the monoclonal antibody.

Yet another object of the invention is to provide a method for sensitively detecting or quantifying an NANBV-related antigen using the monoclonal antibody.

lane 2: lysate of a rabbit kidney culture cell line (RK13) infected with the recombinant vaccinia virus LO-R6J13, approximately $2.5\times10^4$ cells/lane, reducing;

lane 3: lysate of a rabbit kidney culture cell line (RK13) infected with a recombinant vaccinia virus LO-R6J20, approximately $2.5\times10^4$ cells/lane, non-reducing;

lane 4: lysate of a rabbit kidney culture cell line (RK13) infected with the recombinant vaccinia virus LO-R6J20, approximately $2.5\times10^4$ cells/lane, reducing.

Figure 2:
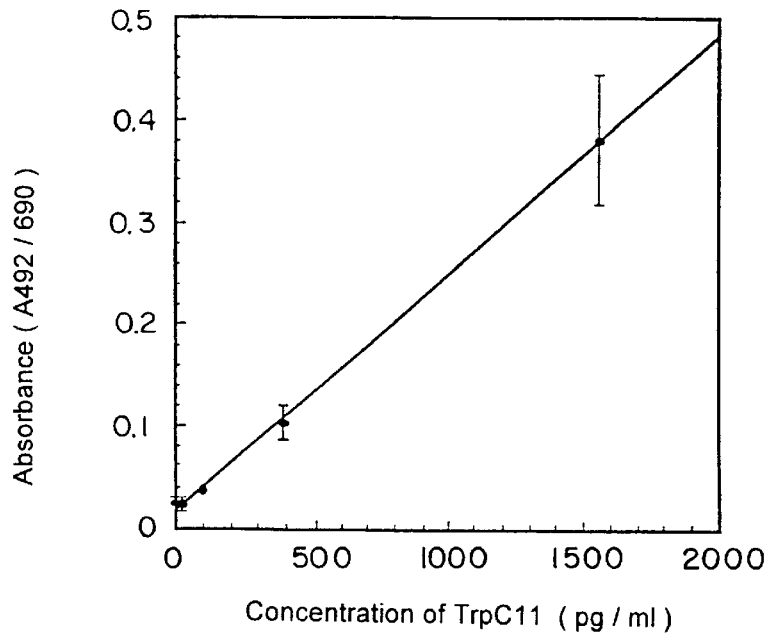

FIG. 2 is a calibration curve of a structural protein TrpC11 derived from NANBV as determined by the sandwitch technique using the monoclonal antibodies 5F11 and 5E3 of this invention. Bars in the figure show 2SD (standard deviation).

Figure 3:
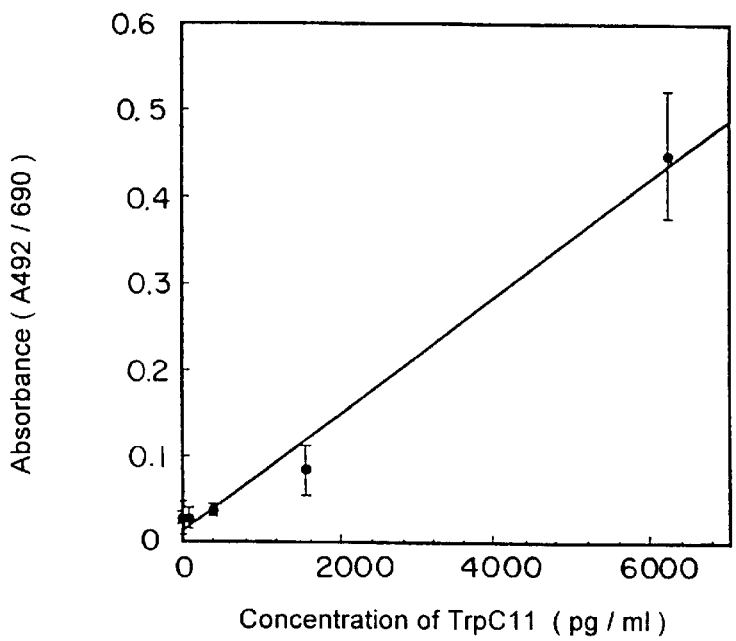

FIG. 3 is a calibration curve of a structural protein TrpC11 derived from NANBV as determined by the sandwitch technique using monoclonal antibodies 1080S and 515S of this invention. Bars show 2SD.

Figure 4:
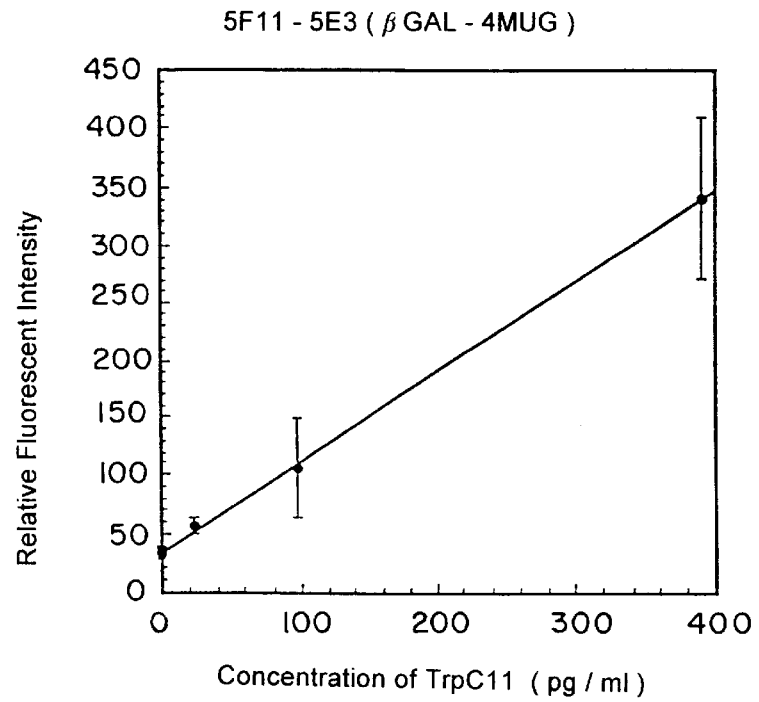

FIG. 4 is a calibration curve of a structural protein TrpC11 derived from NANBV as determined by the sandwitch technique using a solid phase monoclonal antibody 5F11 together with a β-galactosidase (GAL)-labeled 5E3. Bars show 2SD.

Figure 5:
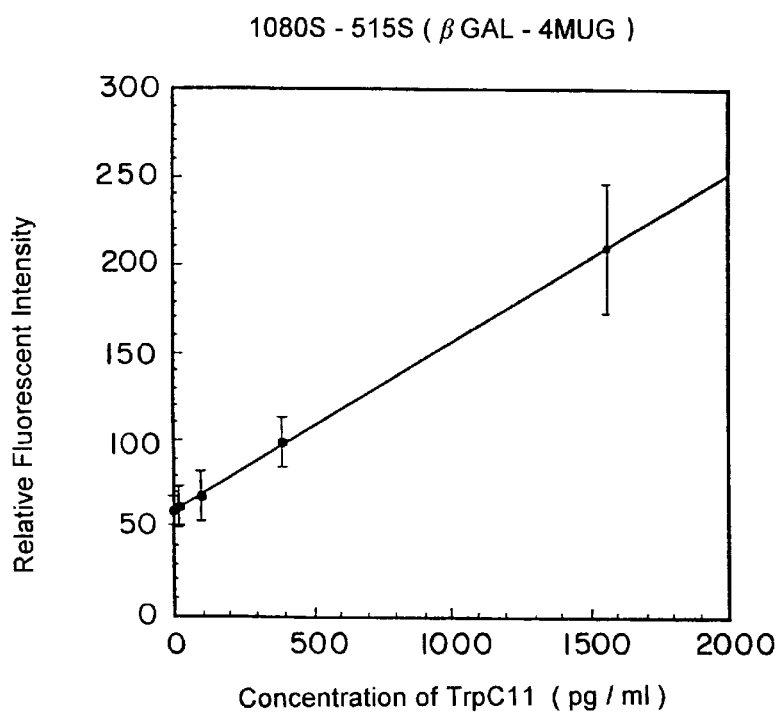

FIG. 5 is a calibration curve of a structural protein TrpC11 derived from NANBV as determined by the sandwitch technique using a solid phase monoclonal antibody 1080S together with a β-galactosidase (GAL)-labeled 515S. Bars show 2SD.

FIG. 6 is a graph showing the detection limit of a structural protein TrpC11 derived from NANBV as determined by the sandwitch technique using the monoclonal antibodies 5F11 and 5E3 of this invention. The concentration of TrpC11 is in the range from 0 to 6,000 pg/ml.

FIG. 7 is a graph showing the detection limit of a structural protein TrpC11 derived from NANBV as determined by the sandwitch technique using the monoclonal antibodies 5F11 and 5E3 of this invention. The concentration of TrpC11 is in the range from 0 to 400 pg/ml.

Figure 8:
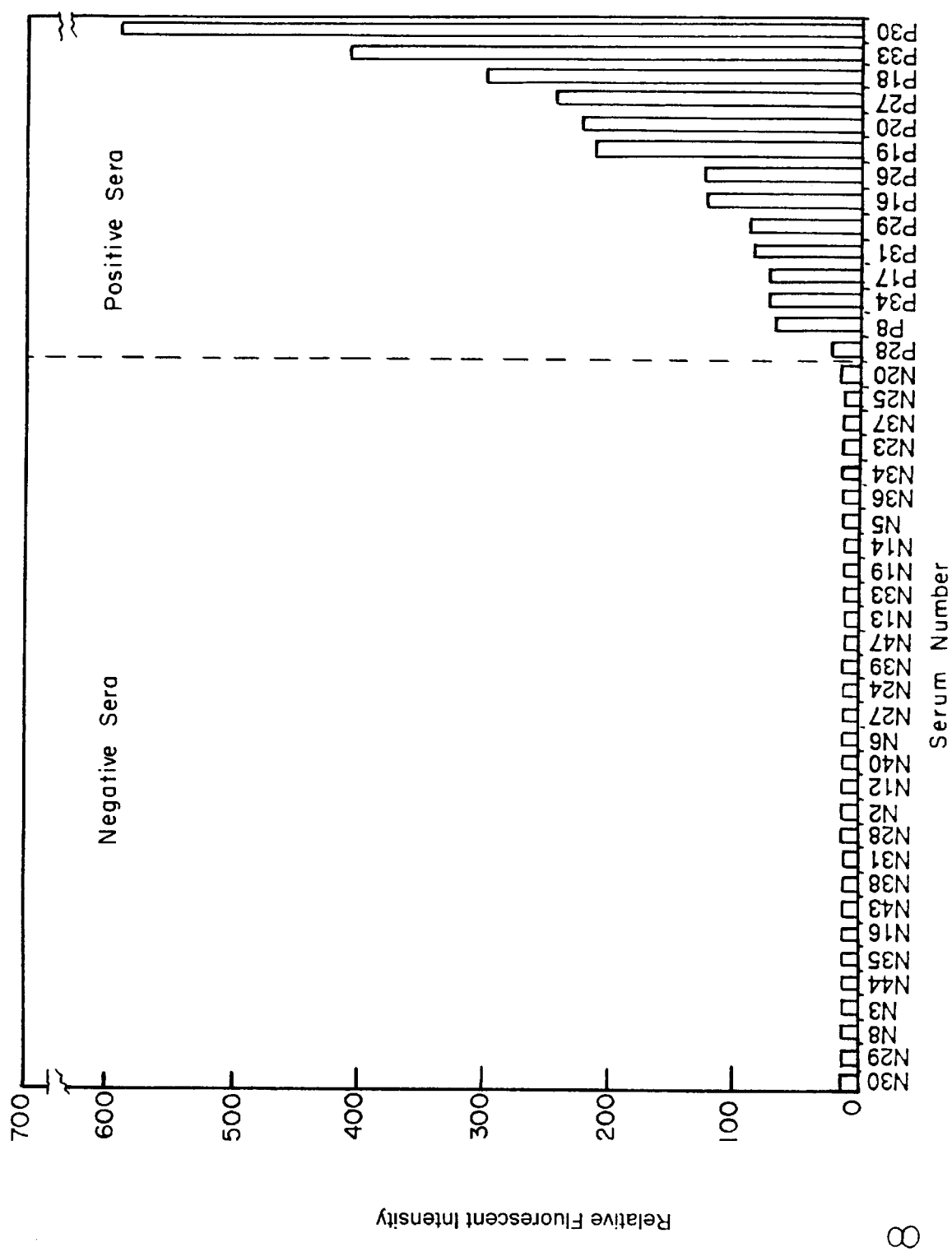

FIG. 8 is a graph showing assay results of NANBV structural proteins in serum samples. Samples having a sample number with "IN" are ones estimated as negative using a commercially available second generation reagent (Immucheck-HCV Ab "KOKUSAI" sold by International Reagents Corp., Japan), and samples having a sample number with "P" are ones estimated as positive using the same.

DETAILED DESCRIPTION OF THE INVENTION

We have studied a method for the detection of antigens from the structural protein region of NANBV by use of monoclonal antibodies against them. As a result, we have now found that NANBV virions could be concentrated and dissociated by centrifuging a specimen (e.g., serum) with polyethylene glycol followed by alkaline treatment of the precipitate obtained. Further, we succeeded in obtaining monoclonal antibodies extremely specific for HCV structural proteins using as immunogens recombinant polypeptides having HCV antigenic activity and prepared by expression of genes for core structural proteins in *Escherichia coli*. The monoclonal antibodies obtained can react specifically with core structural proteins from the viral virion.

Accordingly, this invention provides a monoclonal antibody having a binding specificity for an antigenic determinant site on core structural protein from NANBV.

More specifically, the monoclonal antibody of the invention can be prepared by transforming a host cell with a recombinant vector that carries a gene fragment encoding an NANBV core protein and comprising a base sequence encoding the amino acid sequence shown in SEQ ID NO:1; culturing the transformed host cell to prepare a polypeptide having an NANBV-antigenic activity and having the amino acid sequence shown in SEQ ID NO:1; and applying the polypetide as immunogen to the usual preparation of monoclonal antibodies. The monoclonal antibody can be prepared from a hybridoma cell line produced by infusion of lymphocytes derived from a mouse immunized with the NANBV core structural protein, with myeloma cells, and it can be employed in immunoassay for the detection or quantification of NANBV structural proteins and in a test kit for the detection or quantification.

Accordingly, this invention provides the hybridoma cell line, the immunoassay and the kit as mentioned above.

In addition, this invention provides a monoclonal antibody capable of specifically recognizing an amino acid sequence shown in SEQ ID NO:2, 3, 4 or 5 or its partial sequence; an immunoassay for the detection or quantification of NANBV structural proteins using the monoclonal antibody; and a kit for use in the immunoassay.

The immunoassay of the invention comprises the following steps of: (a) centrifuging a specimen with polyethylene glycol to concentrate Non-A,Non-B hepatitis virus or its related antigens therein, followed by alkaline treatment; (b) contacting the specimen treated in step (a) with the monoclonal antibody of the invention to form an antigen-antibody complex; and detecting or quantifying the presence of NANBV-related antigens.

This assay is characterized by comprising a pretreatment in which a specimen is centrifuged with polyethylene glycol to concentrate NANBV or its related antigens, and the precipitate is then treated with an alkaline agent such as sodium hydroxide, whereby the viral virions are disintegrated and any coexisting antibodies are deactivated. In this invention, the monoclonal antibody possesses a binding constant $K_A$ in forming an immune complex of the monoclonal antibody with an NANBV structural protein: normally $5\times10^7$ [$M^{-1}$] or larger, preferably $5\times10^8$ [$M^{-1}$] or larger, more preferably $7\times10^8$ [$M^{-1}$] or larger.

This invention will be described in more detail.

The term "gene fragment encoding a structural protein of Non-A,Non-B hepatitis virus" as used herein refers to a gene fragment comprising a gene encoding the core region of NANBV structural proteins, namely, a DNA fragment comprising a base sequence encoding a polypeptide having at least an amino acid sequence from position 1 (corresponding to the N-terminus of the entire structural region coded for by the NANBV genome) to position 123. Particularly, it is a gene fragment comprising a base sequence encoding the amino acid sequence shown in SEQ ID NO:2.

The gene fragment in this invention can be prepared from a cDNA library that was prepared through the separation of NANBV genes from sera of patients with post-transfusion Non-A,Non-B hepatitis, or alternatively it can be obtained by synthesizing DNA probes based on known nucleotide sequences of NANBV genes (see Proc. Natl. Acad. Sci. USA, 87:9527–9528, 1990; and ibid, 88:2451–2455, 1991), subjecting the cDNA library to DNA/DNA or DNA/RNA hybridization in accordance with usual methods, and then screening a desired gene fragment.

A fusion gene in this invention can be prepared by ligating together two DNAs, i.e. the gene fragment encoding an NANBV structural protein and TrpE gene, by conventional recombinant DNA techniques. The ligation or fusion may be carried out by utilizing restriction sites from a linker added when the cDNA library is prepared, restriction sites from a plasmid in which the gene fragment is inserted, or the like in the case of the gene fragment, whilst by utilizing restriction sites from a plasmid in which the TrpE gene is inserted or restriction sites present in the TrpE gene in the case of the TrpE gene.

In this invention, recombinant vectors containing the fusion gene can be prepared by insertion of the fusion gene into a vector such as plasmid by usual recombinant DNA techniques. As the vector, in addition to conventional vectors such as plasmids and phages, viruses such as vaccinia virus and baculovirus may be used.

Hosts usable are for example prokaryotes such as *E. coli*, *Bacillus subtilis* or Actinomycetes, and promoters usable in this case are for example tryptophan synthetase operon (trp), lactose operon (lac), λ phage $P_L$ and $P_R$, and so on. In this case, recombinant (poly)peptides can be obtained as infusion with other peptides with good efficiency.

Eukaryotes, e.g. yeast cells, insect cells, plant cells and animal cells, may be employed too. Promoters usable in this case are for example promoters for enzymes such as 3-phosphoglycelate kinase and enolase in the glycolisis system and for alcoholdehydrogenase which promoters can be usually used in yeast cells; and viral promoters usable in mammalian cells such as promoters from Poliomavirus, Adenovirus, simian SV-40, vaccinia virus and Cytomegalovirus, etc.

The vectors as used in the invention may optionally contain a marker sequence such as ampicillin resistance gene or tetracycline resistance gene, an origin of replication, a terminator, a ribosome-binding site, and the like.

The recombinant NANBV structural protein can be prepared, for example, by the process comprising constructing a replicable expression vector capable of expressing the above mentioned gene fragment within an appropriate host cell; introducing the expression vector into the host cell to obtain a transformed cell; culturing the transformed cell under conditions capable of expressing the gene fragment to produce a recombinant (poly)peptide; and recovering the recombinant (poly)peptide.

For the transformation, usual methods including calcium chloride method may be applied. For example, see Examples set forth below where *E. coli* host cells were transformed with a recombinant vector Trp.TrpE CORE140 to obtain a recombinant *E. coli*.

The culture of the transformed *E. coli* can be carried out in a usual eutrophic medium for *E. coli* such as L medium, YT medium or M9-CA medium. The recombinant vector prepared as above has a drug resistance gene, so when the *E. coli* containing the vector is cultured then it is desirable to add to its medium a corresponding drug of an appropriate concentration. For example, when a recombinant *E. coli* strain HB101[Trp.TrpE CORE140] that was obtained by transforming *E. coli* strain HB101 with the recombinant vector Trp.TrpE CORE140 is cultured, ampicillin may be added to the medium in a concentration of 20–200 μg/ml.

The expression of a gene for the fusion polypetide is carried out by inducing the expression by an appropriate promoter upstream of the gene. For example, in the case of the above mentioned vectors, after the transformed host cell is cultured in an appropriate medium until a given level of bacterial cells is obtained, the gene expression can be started by addition of IAA (i.e., indoleacrylic acid). To conduct the efficient gene expression, IAA is preferably added at the early phase or middle phase of the logarithmic growth phase. Following induction of the expression, the culture is continued to accumulate the fusion polypeptide within the bacterial cells. For example, in the case of the recombinant *E. coli* strain HB11[Trp.TrpE CORE140], it is cultured in an ampicillin-containing M9-CA medium at 37° C. for 13–16 hr thereby being obtained in a full amount and producing the fusion polypetide in a high yield.

The collection and purification of fusion polypeptides from cultured bacterial cells can be carried out by conventional techniques, e.g. sonication of the cells, solubilization, ammonium sulfate fractionation, and various chromatographies.

When the fusion polypeptides are expressed efficiently by the above mentioned methods, they form insoluble granules within bacterial cells. In this case the bacterial cells are dispersed in a physiological buffer such as physiological saline and then destructed by for instance sonication, after which the debris is subjected to centrifugation to recover the insoluble materials as precipitate.

The recovered insoluble materials are washed with a buffer containing a low concentration of urea, guanidium HCl or surfactant such as Triton X-100 to obtain a fusion polypeptide having a high purity. The fusion polypetide in the form of insoluble materials can be solubilized by adding thereto a buffer containing 6–8M urea or guanidium HCl. The solubilized fusion ploypeptide can be dialyzed against or dissolved in an appropriate buffer such as physiological saline so as to decrease the level of urea or guanidium HCl up to an appropriate concentration. The resulting fusion polypetide can be employed as immunogen. If the fusion polypetide is needed to purify in a higher purity, it can be purified using known purification procedures, e.g., separation methods such as salting out, ion-exchange chromatography, gelfiltration and affinity chromatography, fractionation method such as electrophoresis, and combinations thereof.

When a certain base sequence encoding an amino acid sequence that can be cleaved chemically or enzymatically is inserted between the gene fragment encoding NANBV structural protein and the TrpE gene, the fusion polypetide produced is treated by appropriate methods whereby the NANBV antigenic polypeptide that comprises the amino acid sequence shown in SEQ ID NO:1 and is coded for by the gene fragment can be obtained in the TrpE-free form. In this invention, if the part of the amino acid sequence shown in SEQ ID NO:1 includes a substitution, insertion or deletion and the antigenic activity of the polypeptide variant is substantially identical to that of the intact polypetide, such a variant is also included in the scope of the invention.

The term "polypeptide having NANBV antigenic activity" as used herein refers to a polypeptide or fusion polypeptide reactive immunologically with an anti-NANBV antibody, and it can be employed as an antigen for use in preparation of hybridomas and monoclonal antibodies. For example, the polypeptide of the invention is a fusion polypeptide having NANBV antigenic activity and comprising the amino acid sequence shown in SEQ ID NO:1, or a polypeptide having NANBV antigenic activity and comprising a part of the amino acid sequence shown in SEQ ID NO:1, wherein to the N- or C-terminus may be added an extra amino acid sequence. As the partial sequence of the amino acid sequence shown in SEQ ID NO:1, preferred are sequences shown in SEQ ID NOs:3, 4 and 5.

Monoclonal antibodies of the invention, directed against the above mentioned fusion polypeptides or polypeptides comprising the amino acid sequence shown in SEQ ID NOs:3, 4 or 5, can be easily prepared. The preparation of a monoclonal antibody by using hybridomas is well known. For example, the following procedures can be employed. BALB/c mice are immunized intraperitonially or subcutaneously at regular intervals of time with each of the above mentioned fusion polypeptides or polypeptides (hereinafter, referred to as "antigen") as a single antigen or as an antigen coupled to BSA, KLH or the like, in combination with complete Freund's adjuvant. At the time when the antibody titer in blood is raised, the mice are boosted with the antigen in the murine tail vein. Following the aseptic removal of spleen cells, they are fused with an appropriate murine myeloma cell line to obtain hybridomas. The preparation method of the monoclonal antibodies of the invention can be carried out by the method of Köhler and Milstein (see Nature 256:495–497, 1975).

Thus, this invention further provides a hybridoma cell line capable of producing a monoclonal antibody having a binding specificity for an antigenic determinant site on the NANBV core structural protein. More particularly, the hybridoma cell line is selected from the group consisting of HC11-5E3, HC11-5F11, HC11-515S and HC11-1080S. Hybridomas HC11-5E3, HC11-5F11, HC11-515S and HC11-1080S were respectively deposited with the national Institute of Bioscience and Human-Technology, Agency of Industrial Science and Technology, Ministry of International Trade and Industry, Japan on Jul. 5, 1994, Jul. 5, 1994, Jun. 29, 1994 and Jun. 29, 1994 under accession numbers FERM P-14415, FERM P-14416, FERM P-14403 and FERM P-14402, and subsequently transferred to the international deposition under the terms of the Budapest Treaty on Jun. 23, 1995 and received Accession Nos. FERM BP-5147, FERM BP-5148, FERM BP-5146 and FERM BP-5145, respectively.

The hybridoma cell lines prepared as above are cultured in an appropriate medium, and thereafter a hybridoma cell line capable of producing an antibody specific for the antigen (i.e., polypeptide or fusion polypeptide described above) is screened for cloning. The cloning of the antibody producing hybridoma can be carried out using the limited dilution method or the soft agar method (see Eur. J. Immunol. 6:511–519, 1979) or the like. The resultant monoclonal antibody can be purified by for example a column chromatography using Protein A.

Thus, this invention further provides a monoclonal antibody produced by the above mentioned hybridoma cell line and having a binding specificity for an antigenic determinant site on the NANBV core structural protein.

Examples of the antigenic determinant site include sequences constituted by at least 3, preferably at least 5, more preferably 8 contiguous amino acid residues in the amino acid sequences shown in SEQ ID NOs:1, 3, 4 and 5. As the monoclonal antibodies used in the invention, preferred are ones having at least $5 \times 10^7$ [$M^{-1}$] of a binding constant $K_A$ in forming an antigen-antibody complex between the monoclonal antibody and the NANBV core structural protein. Particularly, the monoclonal antibodies are selected from the group consisting of 5E3, 5F11, 515S and 1080S that are secreted by the above mentioned specific hybridoma cell lines.

This invention further provides a process for the preparation of the above mentioned monoclonal antibodies, which process comprises fusing a myeloma cell line with lymphocytes derived from a mouse immunized with the NANBV core structural protein to prepare a hybridoma cell line; culturing the resultant cell line while secreting a monoclonal antibody specifically binding to an antigenic determinant site on the NANBV core structural protein; and purifying the resultant monoclonal antibody.

Examples of the immunogens include (poly)peptides having the amino acid sequences shown in SEQ ID NOs:1, 2, 3, 4 and 5, or partial sequences thereof.

Alternatively, the monoclonal antibodies of the invention can be prepared by using phage surface-presenting system (see Nature 348:552–554, 1990; ibid, 349:293–299, 1991). Briefly, the spleen cells are removed from an immunized mouse, from which RNA is prepared by usual methods (including guanidine thiocyanate method or phenol extraction method) and polyA RNA that is a fraction containing mRNA is prepared by usual methods. In this case, the hybridoma cell lines established by the above mentioned methods may be employed in place of the spleen cells. Using the mRNA as template, cDNA is synthesized, after which PCR is carried out using appropriate primers capable of amplifying long chain or short chain variable regions of immunoglobulin to obtain a long chain or short chain variable region-encoding DNA fragment. After the amplified DNA fragments encoding the long chain and short chain variable regions are ligated together by genetic engineering techniques, the resultant ligated DNA is introduced in an expression vector that enables phage surface presenting, e.g. pCANTAB5E (Pharmacia) and expressed in E. coli as host. Of phages in which the variable regions were presented, ones bindable to the polypeptides of interest are chosen, and by using them can be prepared monoclonal antibodies that have an ability capable of binding to the homologous peptides to those produced in murine cells.

The monoclonal antibodies prepared according to the invention can be employed in detection or quantification of NANBV structural proteins in specimens, and as test reagents usable in assays such as enzyme-linked immunosorbent assay (ELISA), enzyme immunodot assay, radioimmunoassay, aggregation-based assay, or other well known immunoassays. In detection, a labeled antibody can in general be employed. Examples of labeling compounds are enzymes, fluorescent substances, chemiluminescent substances, radioactive substances and dye substances, which are known in this field.

Examples of specimens are biological fluids such as whole blood, serum and plasma, liver tissue, etc.

This invention further provides a test kit for the detection or quantification of NANBV or its related antigens in specimens, the kit being able to use in the above mentioned immunoassys. The kit comprises at least one monoclonal antibody, preferably at least two monoclonal antibodies as defined above, and one of the antibodies may be employed as a labeled second antibody.

For example, when two-antibody sandwitch reaction system is used for detection of NANBV structural proteins in specimens, the test kit may comprise a monoclonal antibody of the invention coated onto a solid support (e.g., inner wall of microtiter wells), together with a labeled monoclonal antibody or its fragment as a second antibody. The monoclonal antibodies usable herein are as defined above, and they are preferably selected from the group consisting of 5E3, 5F11, 515S and 1080S. Any combinations of a monoclonal antibody immobilized on a solid support with a labeled monoclonal antibody can be selected as long as the high sensitivity for detection or quantification is achieved.

Examples of solid supports include a microtiter plate, tube or capillary (e.g., made of polystyrene, polycarbonate, polypropylene, polyvinyls, etc.), beads (e.g., latex particles, erythrocytes, metal compounds, etc.), films (e.g., liposomes), and membrane filters.

In this invention, the immunoassay for the detection or quantification of NANBV structural proteins comprises a pretreatment in which each specimen is treated physically and chemically. That is, polyethylene glycol (PEG) is added to a specimen and then dissolved followed by centrifugation, after which the precipitate is denatured by addition of an alkaline solution thereby the NANBV structural proteins in the specimen being concentrated and disintegrated. By this pretreatment, the high sensitive assay can be achieved. The average molecular weight and content of PEG for use in the treatment of sera can be varied. The average molecular weight of PEG used is typically 1,000, 1,500, 2,000, 4,000 or 6,000, and the content thereof is in the range from 3% to 5% (by weight). PEG having an average molecular weight of 1,000 to 2,000 is advantageously employed in a liquid form after heating because it is a gel and its handling is hard. PEG 4,000 and PEG 6,000 are preferably employed in the pretreatment because they are crystals thus leading to easy handling, and therefore the use of these PEGs is one of preferred embodiments in the invention. Examples of the alkaline agent include, but not limited to, alkali metal or alkaline earth metal hydroxides. The pH of the solution is at least pH 10, preferably pH 12 to 14 during the denaturation treatment.

This invention will be illustrated by the following Examples in more detail, but it should be understood that the invention is not limited only by the Examples.

EXAMPLE 1

Expression and Purification of Polypeptide Derived from Non-A,Non-B Hepatitis Virus (A) Construction of expression plasmid An expression plasmid that can express a polypeptide of HCV core region was constructed by the method set forth below. One µg of each DNA of plasmids pUC.C11-C21 and pUC.C10-E12 which were obtained by integrating clones C11-C21 or C10-E12 (see JP-A-6-38765 corresponding to U.S. patent application Ser. No. 08/081,072) into pUC119, respectively, was digested at 37° C. for 1 hr in 20 µl of a restriction reaction solution [50 mM Tris-HCl (pH 7.5), 10 mM MgCl$_2$, 1 mM DTT, 100 mM NaCl, 15 units of EcoRI, and 15 units of ClaI] or [10 mM Tris-HCl (pH 7.5), 10 mM MgCl$_2$, 1 mM DTT, 50 mM NaCl, 15 units of ClaI, and 15 units of KpnI], respectively. Thereafter, the digests were subjected to 0.8% preparative agarose gel electrophoresis to purify approximately 380 bp EcoRI-ClaI and approximately 920 bp ClaI-KpnI fragments. The two DNA fragments were ligated to a vector that pUC119 had been digested with EcoRI and KpnI at 16° C. overnight in 50 µl of a ligase solution which contains a mixture of 5 µl of 10× ligase buffer [660 mM Tris-HCl (pH 7.5), 66 mM MgCl$_2$, 100 mM dithiothreitol, 1 mM ATP] and 1 µl of T4 ligase (350 units/µl) diluted with water to the total volume of 50 µl. E. coli strain JM109 was transformed with the resultant plasmid to obtain a plasmid pUC.C21-E12.

One ng of the plasmid pUC.C21-E12 DNA was subjected to PCR using two primers: 5'-GAATTCATGGGCACGAATCCTAAA-3[1] (SEQ ID NO:6) and 5'-TTAGTCCTCCAGAACCCGGAC-3' (SEQ ID NO:7). The PCR was carried out using GeneAmp™ Kit (DNA Amplification Reagent Kit, Perkin Elmer Cetus) under the conditions: DNA denaturation, 95° C., 1.5 min; annealing, 50 C, 2 min; and DNA synthesis, 70° C., 3 min. A DNA fragment obtained by PCR was separated by 0.8% agarose gel electrophoresis and then purified by Glass Powder method (Gene Clean). On the other hand, after pUC19 was digested with SmaI, the above DNA fragment was ligated to the digested pUC19 at 16° C. overnight in 50 µl of a ligase solution which contains a mixture of 5 µl of 10× ligase buffer [660 mM Tris-HCl (pH 7.5), 66 mM MgCl$_2$, 100 mM dithiothreitol, 1 mM ATP] and 1 µl of T4 ligase (350 units/µl) diluted with water to the total volume of 50 µl. E. coli strain JM109 was transformed with the resultant plasmid to obtain a plasmid pUC.19.C21-E12.SmaI. One µg of this plasmid DNA was digested at 37° C. for 1 hr in 20 µl of a restriction reaction liquid [150 mM NaCl, 6 mM Tris-HCl (pH 7.5), 6 mM MgCl$_2$, 15 units of EcoRI, and 15 units of BamHI], after which the digest was subjected to 0.8% agarose gel electrophoresis to separate an approximately 490 bp EcoRI-BamHI fragment which was then further purified by Glass Powder method.

Next, 1 µg of an expression vector Trp.TrpE DNA (see JP-A-5-84085) was digested at 37° C. for 1 hr in a restriction reaction liquid [150 mM NaCl, 6mM Tris-HCl (pH 7.5), 6 mM MgCl$_2$, 15 units of EcoRI, and 15 units of BamHI]. To the reaction mixture was added 39 µl of water followed by heat treatment at 70° C. for 5 min, after which to this was added 1 µl of bacterial alkaline phosphatase (BAP) (250 units/µl) and the mixture was then left at 37° C. for 1 hr. Following addition of phenol, phenol extraction was conducted, the aqueous layer was ethanol-precipitated, and the precipitate was dried. The resultant EcoRI-BamHI treated vector DNA 1 µg was ligated to the above CORE140 fragment at 16° C. overnight in 50 µl of a ligase solution which contains a mixture of 5 µl of 10× ligase buffer [660 mM Tris-HCl (pH 7.5), 66 mM MgCl$_2$, 100 mM dithiothreitol, 1 mM ATP] and 1 µl of T4 ligase (350 units/µl) diluted with water to the total volume of 50 µl.

E. coli strain HB101 was subsequently transformed with 10 µl of the resultant reaction mixture. This competent E. coli strain for use in transformation was prepared by the calcium chloride method (see Mandel, M. and Higa, A. J. Mol. Biol., 53:159–162, 1970). The transformed E. coli was plated onto a LB plate (1% tryptone, 0.5% NaCl and 1.5% agar) containing 25 µg/ml of ampicillin, and cultured at 37° C. overnight. A colony on the plate was taken in an amount of 1 platinium loop, which was then transferred to LB medium containing 25 µg/ml of ampicillin followed by culture at 37° C. overnight. By using the bacterial cells collected by centrifugation of 1.5 ml of the culture, Mini-Prep of plasmid DNA was carried out by the alkaline method [see Manniatis et al, Molecular Cloning: A Laboratory Manual, (1982)]. The resultant plasmid DNA 1 µg was digested at 37° C. for 1 hr in 20 µl of a restriction reaction liquid [150 mM NaCl, 6 mM Tris-HCl (pH 7.5), 6 mM MgCl$_2$, 15 units of EcoRI, and 15 units of BamHI]. Following agarose gel electrophoresis, an expression plasmid Trp.TrpE CORE140 that can generate an approximately 490 bp EcoRI-BamHI fragment was screened.

(B) Expression and purification of polypeptide encoded by clone CORE140

The *E. coli* strain HB101 carrying the expression plasmid Trp.TrpE CORE140 was inoculated in 3 ml of 2YT medium (1.6% tryptone, 1% yeast extract, 0.5% NaCl) containing 50 μg/ml of ampicillin, and cultured at 37° C. for 9 hr. One ml of the culture was then subcultured at 37° C. in 100 ml of M9-CA medium (0.6% $Na_2HPO_4$, 0.5% $KH_2PO_4$, 0.5% NaCl, 0.1% $NH_4Cl$, 0.1 mM $CaCl_2$, 2 mM $MgSO_4$, 0.5% casamino acids, 0.2% glucose). When $OD_{600}$ reached 0.3, indoleacrylic acid was added to the culture to a final concentration of 40 mg/l, followed by 16-hr culture. The culture was centrifuged to collect bacterial cells.

The bacterial cells were suspended in 20 ml of Buffer A [50 mM Tris-HCl (pH 8.0), 1 mM EDTA, 30 mM NaCl], and subjected to recentrifugation to obtain 2.6 g the expressed bacterial cells which were subsequently suspended in 10 ml of Buffer A and disintegrated by sonication. Following centrifugation, an insoluble fraction that contains a fusion polypeptide of a polypeptide encoded by NANBV cDNA with TrpE was obtained. To this fraction was added 10 ml of Buffer A containing 6M urea to solubilize the fusion polypeptide. The solubilized extract was loaded onto an ion-exchange column and eluted with the gradient from 0M NaCl to 0.5M NaCl to purify the fusion polypeptide.

EXAMPLE 2

Preparation of Hybridoma

The fusion polypeptide (TrpC11) prepared by the method of Example 1 was dissolved in physiological saline in a concentration of 1.0 mg/ml, and then mixed with an equal volume of complete Freund's adjuvant to make a suspension of TrpC11. The concentration of TrpC11 in the suspension was adjusted to the range from 0.01 mg/ml to 0.05 mg/ml, after which the suspension was intraperitoneally administered to 4 to 6-week-old BALB/c mice. After 8 weeks, a physiological saline solution containing 0.01–0.03 mg/ml of TrpC11 was administered in the tail veins of the immunized animals. On day 3 after final booster, the spleen cells were aseptically removed from each immunized animal, sliced with scissors, broken up into individual cells using a mesh, and washed three times with RPMI-1640 medium. After the spleen cells were cultured over several days in the presence of 8-azaguanidine, a murine myeloma cell line PAI of logarithmic growth phase from which back mutations were removed completely was washed as above. This $1.8\times10^7$ myeloma cells were mixed with $1.0\times10^8$ spleen cells in a 50-ml centrifugation tube. Following 5-min centrifugation at 200×g, the supernatant was mixed with 1 ml of RPMI-1640 medium containing 50% polyethylene glycol (PEG) #4000 (Merck) at 37° C. to effect cell fusion between them. The PEG was removed from the fusion cells by centrifugation (200×g, 5 min), and the fusion cells were cultured over 1 to 2 weeks in RPMI-1640 containing hypoxanthine, aminopterin and thymidine (hereinafter, referred to HAT) in a 96-well plate, to result in growth of hybridomas alone. Thereafter, the fusion cells were grown in the HAT-free medium and, after 2 weeks, screened for clones producing antibodies of interest by ELISA to obtain hybridomas capable of producing the monoclonal antibodies of this invention, having desirable specificity.

With respect to the hybridomas obtained, the screening of strains producing monoclonal antibodies of interest was carried out in accordance with the conventional limiting dilution method. As the results, the screened hybridomas were named HC11-5E3, HC11-5F11, HC11-515S and HC11-1080S, all of which were respectively deposited with the National Institute of Bioscience and Human-Technology, Agency of Industrial Science and Technology, Ministry of International Trade and Industry, Japan on Jul. 5, 1994, Jul. 5, 1994, Jun. 29, 1994 and Jun. 29, 1994 under accession numbers FERM P-14415, FERM P-14416, FERM P-14403 and FERM P-14402, and subsequently transferred to the international deposition under the terms of the Budapest Treaty on Jun. 23, 1995 and received Accession Nos. FERM BP-5147, FERM BP-5148, FERM BP-5146 and FERM BP-5145, respectively.

EXAMPLE 3

Preparation of Monoclonal Antibody

The hybridomas obtained in Example 2 were treated with pristane and then planted into murine abdomes, after which monoclonal antibodies produced in ascites were removed from the abdomes. The monoclonal antibodies were purified in accordance with usual procedures: precipitation with ammonium sulfate; dialysis against phosphate buffer; and separation of IgG fraction on Protein A-bound Sepharose column. The sub-types of the monoclonal antibodies 5E3, 5F11, 515S and 1080S produced by the above mentioned 4 types of hybridomas were determined as being IgG2a for 5E3 and 5F11 and IgG1 for 515S and 1080S by the double diffusion method using each of the isotypes of rabbit anti-mouse Ig (Zymed). Regarding 4 types of the monoclonal antibodies, epitope analyses were conducted using 20 peptides synthesized based on sequences from the HCV core region, and as a result, it has been found that they could recognize parts of the core region specifically. The results are shown in Table 1.

TABLE 1

| Antibody | Recognition site |
| --- | --- |
| 5E3 | $^{25}$Pro - $^{35}$Tyr (SEQ ID NO:3) |
| 5F11 | $^{51}$Lys - $^{60}$Gly (SEQ ID NO:5) |
| 515S | $^{25}$Pro - $^{35}$Tyr (SEQ ID NO:3) |
| 1080S | $^{30}$Ile - $^{50}$Arg (SEQ ID NO:4) |

EXAMPLE 4

Demonstration of Reaction Specificity of the Antibodies by Western Blotting

Lysates containing proteins expressed within a culture cell line derived from rabbit kidney, RK13, that has been separately infected with a recombinant vaccinia virus LO-R6J20 which carries a gene encoding CORE, ENV, E2/NS1 and NS2 regions from HCV or with a recombinant vaccinia virus LO-R6J13 which carries a gene encoding ENV and E2/NS1 regions from HCV, were subjected to SDS-polyacrylamide gel electrophoresis, after which the resultant gel was attached closely to a polyvinylidene fluoride membrane (PVDF membrane, Millipore) and electroblotted (gel side: cathode; PVDF membrane side: anode) to transfer the proteins on the gel to the PVDF membrane. Then the transferred PVDF membrane was soaked at 4° C. overnight in 0.1M phosphate buffer (pH 7.4) containing 5% skim milk (Difco) and 1% BSA (bovine serum albumin) in order to effect blocking and washed with Tris-HCl buffer (pH 7.0) containing 0.05% Tween 20 (referred to as "TBS").

The PVDF was subsequently reacted at room temperature for 1 hr with 10 μg/ml of a monoclonal antibody chosen from 515S, 1080S, 5E3 and 5F11, as first antibody, prepared in Example 3 and dissolved in 0.1M phosphate buffer (pH 7.4) containing 5% skim milk and 1% BSA. After reaction, the PVDF membrane was washed well with TBS and then reacted at room temperature for additional 1 hr with a horse radish peroxidase-labeled anti-mouse IgG+IgM antibody mixture, as second antibody, diluted in 0.1M phosphate buffer (pH 7.4) containing 5% skim milk and 1% BSA. After the resultant PVDF membrane was washed well with TBS, the color development was done using 0.1% 4-chloro-1-naphtol solution and 0.2% $H_2O_2$ solution.

Figure 1C:
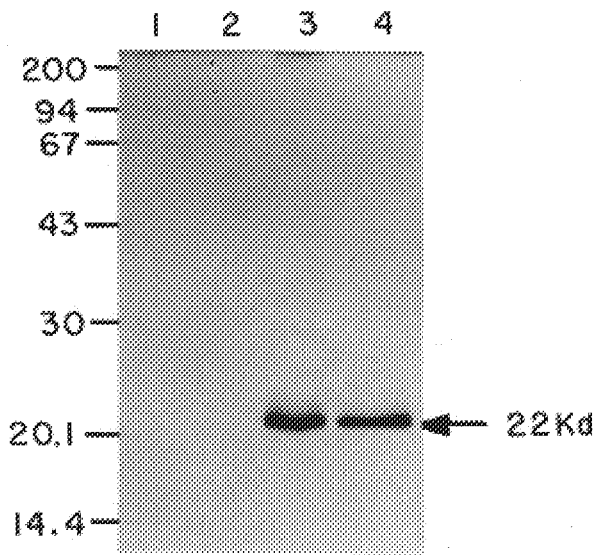
FIG. 1 is a photograph showing Western blot images as results of the immunological reaction between each of the monoclonal antibodies 515S, 1080S, 5E3 and 5F11 and an HCV.CORE antigen, where lane 1: lysate of a rabbit kidney culture cell line (RK13) infected with a recombinant vaccinia virus LO-R6J13, approximately $2.5\times10^4$ cells/lane, non-reducing.
Figure 1D:
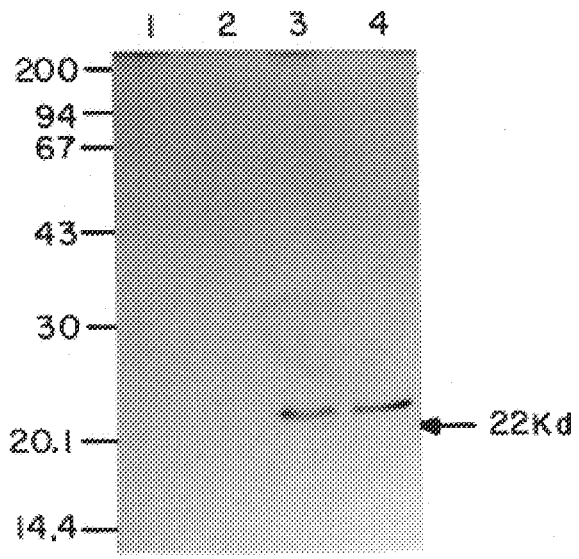

Western blot images between each monoclonal antibody and HCV.CORE antigen are shown in FIG. 1. Each of the monoclonal antibodies was specifically reacted with a 22 Kd protein expressed in the recombinant vaccinia virus-infected eukaryote cells that contain an HCV.CORE region encoding gene, but not with proteins expressed in the recombinant vaccinia virus-infected eukaryote cells that contain a gene encoding HCV.ENV and E2/NS1 regions. Thus these results prove that the monoclonal antibodies employed can recognize an HCV.CORE antigen specifically.

EXAMPLE 5

Preparation of β-galactosidase Labeled Monoclonal Antibody (A) Preparation of 5E3F(ab')$_2$ To use an anti-HCV.CORE antibody (i.e., mouse monoclonal antibody: 5E3IgG) for labeling, 10 mg of the antibody was dialyzed against 0.1M sodium acetate buffer (pH 4.0) containing 0.2M NaCl, and then concentrated to a volume of 1 ml by centrifugation using Centricon™ 10 (Amicon). To the antibody solution was added pepsin (Sigma) suspended in 0.1M sodium acetate buffer (pH 4.0) containing 0.2M NaCl, to a final concentration of 4% based on the total amount of IgG, followed by reaction at 37° C. for 1.5 hr. After the reaction, the reaction mixture was applied to a Sephadex™ G-150 column (φ1.6×60 cm, Pharmacia) equilibrated with 0.1M sodium borate buffer (pH 8.0) to collect an F(ab')$_2$ fraction. After the fraction was dialyzed against 0.1M sodium phosphate buffer containing 1 mM EDTA, it was concentrated to a volume of 1 ml by centrifugation using Centricon™ 10. The concentrate was named 5E3F(ab')$_2$ and used for preparation of a labeled antibody. By this method, about 5 mg of the F(ab')$_2$ could be prepared from 10 mg of 5E3 IgG.

(B) Preparation of β-galactosidase labeled 5E3 antibody

To 5 mg of the 5E3F(ab')$_2$ prepared by the above mentioned method was added 0.1 ml of a solution of 0.1M 2-mercaptoethylamine HCl (Okishida Chemicals, Japan) in 1 mM EDTA plus 0.1M sodium phosphate buffer (pH 6.0), and the mixture was reacted at 37° C. for 90 min. The Fab' was then purified by a column chromatography on Sephadex™ G-25 (φ1.5×20 cm, Pharmacia) equilibrated with 0.1M sodium phosphate buffer (pH 6.0) plus 1 mM EDTA. The Fab' fraction was collected and concentrated to a volume of 1 ml by centrifugation.

On the other hand, β-galactosidase (Boehringer) was weighed (10 mg as protein) and dissolved in 1 ml of 0.1M sodium phosphate buffer (pH 6.0). To this solution was added 10 μl of a solution of 50 mg/ml N,N'-(1,2-phenylene)bismaleimide (Wako Pure Chemicals, Japan) in N,N-dimethyl formamide (Okishida Chemicals, Japan), and the mixture was then subjected to the 20-min maleimidation reaction of the SH group of β-galactosidase at 30° C. The reaction mixture was applied to a Sephadex™ G-25 column (φ1.5×20 cm) equilibrated with 0.1M sodium phosphate buffer (pH 6.0) to collect β-galacosidase fractions which were subsequently concentrated by centrifugation using Centircon™ 10.

The 5E3 Fab' and β-galactosidase prepared as above were mixed in a molar ratio of about 4:1 and reacted at 4° C. for 15–24 hr. Two mM 2-mercaptoethylamine HCl was added to the above reaction mixture to react at 4° C. for 15–24 hr for blocking of unreacted maleimide groups. Then, the unreacted 5E3Fab' was removed by elution using a Sepharose™ 6B column (φ1.6×65 cm, Pharmacia) equilibrated with 10 mM sodium phosphate buffer (pH 6.7), 0.1M NaCl, 0.1% BSA, 1 mM $MgCl_2.6H_2O$ and 0.1% $NaN_3$ (hereinafter, referred to as "Buffer A"), to purify the β-galactosidase labeled 5E3 antibody.

(C) Assay of β-Galactosidase

The activity of β-galactosidase was conducted by Rate Assay. In this assay, 50 μl of the labeled antibody prepared in (B) was added to 2.93 ml of a mixture of 0.3 ml of 10 mM $MgCl_2$, 0.4 ml of 2-nitrophenyl-β-D-galactopyranoside (final concentration, 5.9 mg/ml; Wako Pure Chemicals, Japan) in 50 mM Potassium phosphate buffer (pH 7.8) and 30 μl of 10M mercaptoethanol (Wako Pure Chemicals), in 50 mM potassium phosphate buffer (pH 7.8), to read the difference of absorbance (ΔAbs) at 405 nm at 37° C. over 5 min.

EXAMPLE 6

Preparation of Solid Phase

The anti-HCV.CORE antibody (mouse monoclonal antibody: 5F11 IgG) was diluted to a final concentration of 2.5 μg/ml in 0.1M sodium phosphate buffer (pH 7.5) containing 0.1% $NaN_3$, and the mixture was dispensed into solid phase tubes (Nunc, Startube™) in 300-μl portions per tube. After each tube was left at 4° C. overnight, it was washed twice with 2 ml of 10 mM sodium phosphate buffer (pH 7.0) containing 0.15M NaCl and 0.05% Tween 20 (hereinafter, referred to as "Washing buffer"), added 2 ml of 10 mM sodium phosphate buffer (pH 7.0) containing 0.5% casein-Na and 1% sucrose (hereinafter, referred to as "Blocking buffer"), and left at 4° C. overnight. The tubes prepared as above were employed for assays set forth below.

EXAMPLE 7

Treatment of Sera

One ml of serum was dispensed into a microcentrifugation tube (Eppendorf), and to this was added 40 mg of polyethylene glycol (PEG) 4,000 (Wako Pure Chemicals, Japan). After the tube was overturned repeatedly to well mix the content of the tube, it was left at 4° C. for 3 hr. Following 1-hr centrifugation at 4,000×g at 4° C., the supernatant was removed while the precipitate was suspended in 100 μl of a mixture of 0.5% NaCl and 0.5% of sodium citrate and then subjected to the denaturation reaction at 37° C. for 30 min, after which the reaction mixture was neutralized by addition of 100 μl of 0.5M $NaH_2PO_4$ containing 5% Triton X-100.

EXAMPLE 8

Detection and Quantitative Analysis of Non-A,Non-B Hepatitis Structural Region Core Proteins by Use of the Monoclonal Antibodies 5F11 and 5E3

According to the method described in Example 6, the monoclonal antibody 5F11 was immobilized on a microplate to which Blocking buffer was then added and left at 4° C. overnight, thereby a 5F11 immobilized support being prepared. To each well of the plate were added 100 μl of 10 mM sodium phosphate buffer (pH 7.0) containing 0.5M NaCl, 2.5 mM EDTA.2Na, 1% BSA, 0.5% casein-Na, 5% mouse serum and 0.25% Tween 80 (hereinafter, referred to as "Reaction buffer") and 50 μl of each of the solutions of TrpC11 protein having different concentrations ranging from 0 to 100 ng/ml prepared in Example 1, and the plate was reacted at room temperature for 1 hr while shaking and washed six times with 300 μl each of Washing buffer. The plate was then reacted at room temperature for 1 hr following the addition of 100 μl of the peroxydase (POD) labeled monoclonal antibody 5E3.

After the plate was washed six times with 300 μl of Washing buffer, to which 100 μl of a solution of the substrate o-phenylene diamine (hereinafter, referred to as "OPD") was added, and the plate was reacted at room temperature for 30 min. To the plate, 100 μl of a reaction termination liquid of 2N sulfuric acid was added, after which the amount of TrpC11 protein was determined by measurement of the absorbance ($A_492$) at 492 nm in relative to the absorbance at 690 nm as control. Table 2 shows that the amount of TrpC11 protein can be measured in a dose dependent manner. Thus, by use of the monoclonal antibodies 5F11 and 5E3 of the invention, NANBV structural region core proteins can be detected or determined quantitatively.

EXAMPLE 9

Detection and Quantitative Analysis of Non-A,Non-B Hepatitis Structural Region Core Proteins by Use of the Monoclonal Antibodies 1080S and 515S The TrpC11 protein was measured by repeating the procedure of Example 8, except that the monclonal antibody 1080S and the monoclonal antibody 515S were employed as a solid phase antibody and as a labeled antibody, respectively. As shown in FIG. 3, it is found that the TrpC11 protein can be measured in a dose dependent manner. This result proves that the use of the monoclonal antibodies 1080S and 515S make it possible to detect or quantitatively determine NANBV structural region core proteins.

EXAMPLE 10

Comparison of Sensitivity for Measurement of Non-A,Non-B Hepatitis Virus Structural Region Core Proteins by Means of Different Enzyme-Labeled Antibodies The measurement of the TrpC11 protein was substantially carried out in the same way as in Example 8, except that POD, alkaline phosphatase or β-galactosidase was employed as an enzyme for labeling of second antibodies and that OPD (o-phenylene diamine), HPPA (3-(4-hydroxyphenyl)propionic acid), pNPP (p-nitrophenyl phosphate), NADP (nicotineamide adenine dinucleotide phosphate), AMPPD (3-(2'-spiroadamantane)-4-methoxy-4-(3"-phosphoryloxy)-phenyl-1,2-dioxetane) or 4MUG (4-methylumbelliferyl β-D-galactopyranoside) was employed as a substrate. When a combination of the monoclonal antibodies 1080S and 515S was employed, as seen in Table 2, the system of β-galactosidase/4MUG gave the highest sensitivity for detection of NANBV structural region core proteins. And the high sensitivity was achieved when the monoclonal antibody 5F11 was employed as a solid phase antibody while the β-galactosidase-labeled monoclonal antibody 5E3 as a second aontibody (see FIGS. 4 and 5).

TABLE 2

| | | Detection limit | |
|---|---|---|---|
| Enzyme | Substrate | Enzyme | TrpC11 |
| POD | OPD (colorimetry) | 30 amol/assay | 1,560 pg/ml |
| POD | HPPA (fluorometry) | 15 | 1,000 |
| ALP | pNPP (colorimetry) | 30 | 20,000 |
| ALP | NADP (colorimetry)) | 10 | 1,000 |
| ALP | AMPPD (luminescence method) | 0.2 | 6,000 |
| β-Gal | 4MUG (fluorometry) | 0.5 | 400 |

EXAMPLE 11

Detection Limit of Non-A,Non-B Hepatitis Virus Structural Region Core Proteins in the Case that the Monoclonal Antibodies 5F11 and 5E3 are Employed To the solid phase (plate) immobilized by the antibody 5F11 was added 200 μl of Reaction buffer following the removal of Blocking buffer, then 100 μl of each of the solutions of the TrpC11 protein prepared in Example 1 having different concentrations ranging from 0 to 5,120 pg/ml being added to each well of the plate. The plate was subsequently reacted at 37° C. for 10 min while shaking and washed twice with 2 ml each of Washing buffer. To the plate was added 300 μl of a solution of the 40 mU/ml β-galactosidase-labeled 5E3 diluted in Buffer A followed by 9-min reaction at 37° C. After the plate was washed with 2 ml of Washing buffer, 2 ml of fresh Washing buffer was added and the reaction was carried out at 37° C. for 1 min. The liquid was removed from each well of the plate by suction, and the plate was again washed with 2 ml of washing buffer.

Next, following the addition of 300 μl of a substrate solution: 0.1 mM 4-methylumbelliferyl β-D-galactopyranoside (4MUG; Molecular Probe) diluted in 10 mM sodium phosphate buffer (pH 7.0), 0.15M NaCl, 1 mM $MgCl_2$, 0.1% $NaN_3$ (hereinafter, referred to as "4MUG-dilution buffer")), the reaction was carried out at 37° C. for 9 min while shaking and stopped by addition of 1 ml of 0.1M glycine-NaOH (pH 10.3) (referred to as "Reaction-stop solution). The β-galactosidase labeled 5E3 in well can cleave 4MUG to generate a fluorescent coumarin product. Through the measurement of a relative fluorescent strength of the coumarin product, the concentration of TrpC11 protein can be determined indirectly.

The fluorescent intensity was determined at 360 nm for excitation and 450 nm for emission. As a fluorescent standard was employed a solution of 10 nM 4-methylumbelliferon (Nakarai Chemicals, Japan) in 0.1M glycine-NaOH (pH 10.3), and its ralative fluorescent intensity was set at 100 while that of the 0.1M glycine-NaOH (pH 10.3) at 0.

As shown in FIGS. 6 and 7, the detection limit of TrpC11 was in a level ranging 5 pg/ml to 20 pg/ml.

EXAMPLE 12

Measurement of Non-A,Non-B Hepatitis Virus Structural Region Core Proteins in Serum Samples The quantitative analysis of NANBV structural region core proteins in sera was carried out. The serum samples used were ones identified previously as positive or negative by a second generation diagnostic reagent (Immucheck-HCV Ab "KOKUSAI", sold by International Reagents Co., Japan) for Non-A,Non-B hepatitis and determined as being $10^4$–$10^6$/ml of a PCR-titer by the RT (Reverse Transcriptase) -PCR method. To the 5F11-immobilized solid phase (plate) prepared by the method of Example 6, from which the Blocking buffer has been removed, was added 200 μl of Reaction buffer. Following addition of 100 μl of the serum that was pretreated in the same way as in Example 7, the reaction was carried out at 37° C. for 10 min while shaking. The plate was twice with 2 ml each of Washing buffer, to which 300 μl of a solution of 40 mU/ml β-galactosidase-labeled 5E3 in Buffer A was added followed by 9-min reaction at 37° C. The plate was washed with 2 ml of Washing buffer, and to this was added 2 ml of fresh Washing buffer. After the plate was shaked at 37° C. for 1 min, the liquid was removed by suction. Then the plate was washed with 2 ml of Washing buffer.

To the plate was added 300 μl of a solution of 4MUG in the 4MUG-dilution buffer, and the reaction was carried out at 37° C. for 9 min while shaking, and then stopped by addition of 1 ml of Reaction-stop solution to measure the relative fluorescent intensity at excitation 360 nm and emission 450 nm. As a fluorescent standard, a solution of 10 nM 4-methylumbelliferon (Nakarai Chemicals, Japan) in 0.1M glycine-NaOH (pH 10.3) was employed. Its relative fluorescent intensity was set at 100 while that of the 0.1M glycine-NaOH (pH 10.3) at 0. The recombinant antigen (TrpC11 protein) expressed in Example 1 was used as a standard antigen, and it was dissolved to a concentration of 1 mg/ml in 0.1M sodium phosphate buffer (pH 7.5) plus 8M urea and then adjusted to a given concentration using Reaction buffer. This solution was employed as a standard antigen. As seen in FIG. 8, the test results showed good consistency with those determined using the second generation diagnosis reagent for Non-A,Non-B hepatitis.

EXAMPLE 13

Measurement of Reaction Rate Constants of the Monoclonal Antibodies 5F11, 5E3, 1080S and 515S Rate constants of the immunological reaction between each of the monoclonal antibodies SF11, 5E3, 1080S and 515S and TrpC11 protein were determined using a surface plasmon reasonance analyzer (BIAcore™, Pharmacia) that was an instrument for measurement of biospecific interactions based upon the principle of surface plasmon resonance. The TrpC11 protein was immobilized onto Sensortip™ CM5 (Pharmacia) having a carboxydextran layer by the usual amine coupling method, and each of the monoclonal antibodies that were diluted to an appropriate concentration in HBS buffer (10 mM HEPES, 3.4 mM EDTA, 150 mM NaCl, 0.005% Tween 20, pH 7.4) was flowed through the Sensortip over 25 min. In this case, the resonance signal value that increases by binding of each antibody to the TrpC11 protein on Sensortrip, was measured at time intervals of 30 sec. At the same time, the change in resonance signal was calculated and recorded. The samples were prepared in 5 to 10 different concentrations per antibody and measured in the same way as above to determine an affinity rate constant.

On the other hand, for the measurement of a dissociation rate constant, 100 μg/ml monoclonal antibody in HBS buffer was flowed through the TrpC11 immobilized Sensortip over 15 min to bind the antibody to the TrpC11 on Sensortip. HBS buffer was then passed through the Sensortip over 50 min, and the change in resonance signal resulted from the dissociation of the antibody from the TrpC11 on Sensortip was measured at time intervals of 60 sec. From the ratio of the affinity rate constant and dissociation rate constant determined in the same way as above, the binding constant was calculated. The results are shown in Table 3.

TABLE 3

| Antibody | Affinity rate constant $K_{+1}$ ($M^{-1}s^{-1}$) | Dissociation rate constant $k_{-1}$ ($s^{-1}$) | Binding constant $K_A$ ($M^{-1}$) |
|---|---|---|---|
| 5E3 | $2.2 \times 10^5$ | $<10^{-5}$ | $>2.2 \times 10^{10}$ |
| 5F11 | $4.1 \times 10^4$ | $5.7 \times 10^{-5}$ | $7.2 \times 10^8$ |
| 515S | $8.1 \times 10^4$ | $<10^{-5}$ | $>8.1 \times 10^9$ |
| 1080S | $1.9 \times 10^5$ | $2.3 \times 10^{-4}$ | $8.3 \times 10^8$ |

From the table, all the tested monoclonal antibodies have a binding constant of not less than $10^8$ ($M^{-1}$), indicating that they have high affinity for the target antigen.

Advantages of the Invention

According to this invention, hybridoma cell lines that can produce a monoclonal antibody having high binding specificity for an antigenic determinant on NANBV core structural proteins were obtained. The valuable monoclonal antibodies can specifically recognize the NANBV structural proteins in sera from patients with Non-A,Non-B hepatitis thereby being served extensively as antibodies in various immunological reagents for diagnosis of Non-A,Non-B hepatitis. Additionally, the definitive diagnosis of Non-A, Non-B hepatitis can be conducted by utilizing the detection or quantification method of NANBV with the monoclonal antibodies of the invention.

What is claimed:

1. A hybridoma cell line which is selected from the group consisting of HC11-5E3 (FERM BP-5147), HC11-5F11 (FERM BP-5148), HC11-515S (FERM BP-5146) and HC11-1080S (FERM BP-5145).

2. A monoclonal antibody produced by the hybridoma cell line according to claim 1.

3. An immunoassay of an NANBV-related antigen in a specimen which comprises the following steps:

(a) centrifuging the specimen with polyethylene glycol to concentrate NANBV or its related antigen therein, followed by alkaline treatment;

(b) contacting the specimen treated in the step (a) with a monoclonal antibody produced by a hybridoma selected from the group consisting of HC11-5E3, HC11-5F11, HC11-515S and HC11-1080S to form an antigen-antibody complex; and (c) detecting or quantifying the presence of the NANBV-related antigen.

4. The immunoassay of claim 3 which further comprises labeling the monoclonal antibody.

5. A test kit for use in an immunoassay of an NANBV-related antigen in a specimen, which comprises at least one monoclonal antibody produced by a hybridoma selected from the group consisting of HC11-5E3, HC11-5F11, HC11-515S and HC11-1080S.

6. The test kit of claim 5 which further comprises a labeled secondary monoclonal antibody derived from said monoclonal antibody, wherein the primary and secondary monoclonal antibodies may be identical or different from each other.

7. The test kit of claim 6 wherein said primary monoclonal antibody is selected from the group consisting of 5E3, 5F11, 515S and 1080S which have a binding specificity for an antigenic determinant site on a NANBV core structural protein, and said labeled secondary monoclonal antibody is selected from the group consisting of labeled 5E3, 5F11, 515S and 1080S.

\* \* \* \* \*

UNITED STATES PATENT AND TRADEMARK OFFICE
CERTIFICATE OF CORRECTION

PATENT NO. : 5,871,904
DATED : February 16, 1999
INVENTOR(S) : Tomiko Kashiwakuma et al.

It is certified that error appears in the above-identified patent and that said Letters Patent is hereby corrected as shown below:

On the title page, item [54] and column 1, line 1.
replace "IMMUNASSAY" with --IMMUNOASSAY--.

Signed and Sealed this

Ninth Day of May, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,871,904
DATED : February 16, 1999
INVENTOR(S) : Tomiko Kashiwakuma et al.

It is certified that error appears in the above-identified patent and that said Letters Patent is hereby corrected as shown below:

On title page, Item [73] Assignees
replace "Reagent"
with --Reagents--.

Signed and Sealed this

Sixth Day of June, 2000

Attest:

Q. TODD DICKINSON

*Attesting Officer*                *Director of Patents and Trademarks*